US008043249B2

(12) United States Patent
Covino et al.

(10) Patent No.: US 8,043,249 B2
(45) Date of Patent: Oct. 25, 2011

(54) FIXING DEVICE FOR INJECTION NEEDLES

(75) Inventors: Gian-Carlo Covino, Liestal (CH);
Patrick Fiechter, Huttwil (CH); Fritz Kirchhofer, Sumiswald (CH);
Hans-Ulrich Lehmann, Trachselwald (CH); Daniel Scheidegger, Fraubrunnen (CH); Stefan West, Schliern b. Koeniz (CH)

(73) Assignee: TecPharma Licensing AG, Burgdorf (CH)

( * ) Notice: Subject to any disclaimer, the term of this patent is extended or adjusted under 35 U.S.C. 154(b) by 2129 days.

(21) Appl. No.: 10/782,735

(22) Filed: Feb. 19, 2004

(65) Prior Publication Data
US 2004/0186443 A1    Sep. 23, 2004

Related U.S. Application Data

(63) Continuation of application No. PCT/CH02/00408, filed on Jul. 22, 2002.

(30) Foreign Application Priority Data

Aug. 21, 2001    (CH) ....................... 1543/01

(51) Int. Cl.
*A61N 1/30*    (2006.01)

(52) U.S. Cl. .......................................................... 604/19
(58) Field of Classification Search .................. 604/410, 604/411, 412, 413, 414, 415, 416, 88, 905, 604/19; 606/169, 170, 171; 600/437, 439, 600/471
See application file for complete search history.

(56) References Cited

U.S. PATENT DOCUMENTS

| | | | | |
|---|---|---|---|---|
| 2,828,743 | A * | 4/1958 | Ashkenaz et al. | 604/193 |
| 2,894,509 | A | 7/1959 | Bednarz | |
| 3,344,787 | A | 10/1967 | Maclean | |
| 4,936,841 | A * | 6/1990 | Aoki et al. | 604/413 |
| 5,137,524 | A * | 8/1992 | Lynn et al. | 604/533 |
| 5,445,631 | A * | 8/1995 | Uchida | 604/412 |
| 5,611,786 | A | 3/1997 | Kirchhofer | |
| 6,558,365 | B2 * | 5/2003 | Zinger et al. | 604/410 |
| 6,575,955 | B2 * | 6/2003 | Azzolini | 604/411 |
| 6,656,433 | B2 | 12/2003 | Sasso | |
| 6,875,205 | B2 * | 4/2005 | Leinsing | 604/414 |

FOREIGN PATENT DOCUMENTS

GB    737676    9/1955

\* cited by examiner

*Primary Examiner* — Manuel A Mendez
(74) *Attorney, Agent, or Firm* — Dorsey & Whitney LLP; David E. Bruhn, Esq.

(57) ABSTRACT

A device for connecting an injection needle to an injection apparatus, wherein the device provides a plurality of possible points of contact in at least two planes, and wherein the points of contact have associated spring forces for acting generally perpendicularly on the injection apparatus.

21 Claims, 2 Drawing Sheets

FIXING DEVICE FOR INJECTION NEEDLES

CROSS-REFERENCE TO RELATED APPLICATION(S)

This application is a continuation of International Application No. PCT/CH02/00408, filed on Jul. 22, 2002, which claims priority to Swiss Application No. 1543/01, filed on Aug. 21, 2001, the contents of both are incorporated herein by reference.

BACKGROUND

In ambulatory medicine, reusable injection apparatus or devices for subcutaneously administering liquid medicines are increasingly being used instead of disposable syringes.

One example of such reusable injection apparatus is injection pens which dispense a medicine in a desired amount from a pre-filled ampoule by means of a dosing means. Typically, for each injection, a new injection needle is placed on the injection pen and removed after it has been used. The needle is a hollow needle for conducting medicine from a storage container into the user's or patient's body.

Despite certain standards for injection apparatus, manufacturers prefer to develop injection apparatus which are only suitable specifically for their medicines. Thus, practically all such injection apparatus have a specific fixing device for the needle, which therefore does not fit or only insecurely fits onto another model or device. The needle is securely fixed on an injection pen when it neither slips nor tilts out of the perpendicular. An insecurely fixed needle increases the risk of injuries or needle breakage. If a physician or patient requires a number of medicines or injection apparatus for a treatment, they are furthermore reliant on a corresponding variety of needles, which makes the needles more difficult to obtain and store and, in smaller amounts, makes them more expensive.

Consequently, a fixing device has been sought for injection needles which securely and detachably fixes a needle on different models of injection apparatus, in particular on standard commercial injection pens having a thread or thread segments for detachably fixing or connecting the needle.

Fixing devices for injection needles, for pushing or screwing the needle onto the thread or thread segment, are known from documents WO 95/01812 and GB 737,676. A typical fixing device has the shape of a cap with one open end and one closed end which holds the needle perpendicularly in the middle. At least one elevation or recess, for example a cam, thread or thread segment, is situated on the inner side of the surface areas of the cap and snaps into the flight of the complementary thread or thread segment of the injection pen or is screwed in by being turned. The fixing devices of the above-cited patent specifications typically have cams which taper towards the thread with a pitch which is adapted to the thread, such that—when pushed onto a thread with a different pitch—the cap undesirably tilts out of the perpendicular if the cams engage with the flight.

To prevent tilting, at least three points of contacts are needed between the inner side of the cap or its cams and the thread of the injection pen, wherein said points of contacts are not in the same plane and furthermore hold the cap in the perpendicular. This means that, once pushed on, these points of contacts must no longer shift, otherwise the needle slips along the direction of the needle.

Although not provided for injection pens, U.S. Pat. Nos. 2,894,509 and 2,828,743 describe fixing devices comprising cams or grooves, which—independently of the pitch of the thread—are not in the same plane and enable two fixed positions and a defined shift of a needle. However, the solution from U.S. Pat. No. 2,828,743, with grooves which practically encompass the whole circumference, is not suitable for detachably pushing or screwing onto a thread. The solution from FIGS. 2 and 3 of U.S. Pat. No. 2,894,509 is only suitable for a thread or thread segments if the cams engage uniformly, secured against slipping, with the flights, which given the different dimensions of the threads is rarely the case.

In specific cases, the cap can also tilt out of the perpendicular, the upper or lower pair of cams describing a tilt axis. Consequently, more cams would be necessary to counteract this tilting symmetry. More cams furthermore provide the advantage that, through more points of contact, the clamping force in these points can be smaller for the same adherence of the cap or needle on the injection pen. The clamping force corresponds to a spring force which is predominantly determined by the geometry of the cams, the arrangement on the surface area of the cap and the elasticity of the materials. A smaller clamping force therefore allows, for the same spring force, a larger spring path of the cam or the surface area of the cap. Consequently, such a cap would fit onto correspondingly larger or smaller thread diameters, providing the clamping force always acts the same way, preferably perpendicularly, on the thread of the injection pen.

None of the known fixing devices for injection needles show a solution in which the spring forces in the points of contact always act the same way, in particular perpendicularly, on the thread, if the spring path is increased. This would be the case if the cams were attached in the middle of spring-elastic elements which were each connected to the rigid surface area via an end, analogously to a three-point bending element. Doubling the points of contact, in order to enable a larger spring path of the cams for equally larger differences in the diameters of the threads, required as least twice as much space on the inner side of the surface area of the cap. In the known solutions, with up to five cams at most, this is a very complicated design or cannot be solved at all, when the cams have to be arranged in different planes if the cap is not to tilt out of the perpendicular.

SUMMARY

An object of the present invention is to provide a fixing device for injection needles comprising at least six possible points of contact in at least two planes, wherein the spring forces in the points of contact preferably always act perpendicularly on the thread of the injection apparatus, so that the needle fits securely onto a number of models of injection pens.

In one embodiment, the present invention comprises a device for connecting an injection needle to an injection apparatus, wherein the device provides a plurality of possible points of contact in at least two planes, wherein the points of contact have associated spring forces for acting generally perpendicularly on the injection apparatus.

In one embodiment, the present invention comprises a fixing device for an injection needle comprising a plurality of possible points of contact in at least two planes, wherein the points of contact have associated spring forces, the spring forces acting generally perpendicularly on a thread associated with an injection apparatus, so that the needle may be coupled securely to the injection apparatus.

In one embodiment, the present invention comprises a fixing device for an injection needle comprising at least six possible points of contact in at least two planes, wherein the points of contact have associated spring forces, the spring forces acting generally perpendicularly on a thread associated with an injection apparatus, so that the needle may be coupled securely to the injection apparatus.

The invention relates to a fixing device for injection needles, for pushing onto a thread of an injection apparatus, wherein said fixing device is formed as a cap comprising an open end and a closed end which holds a needle perpendicularly in the middle, and a surface area of the fixing device is spring-elastic in its circumference.

In one embodiment, the fixing device for injection needles in accordance with the present invention has at least three cams having tips that taper towards the thread and which each comprise at least one notch arranged parallel to the surface circumference, whereby each cam has at least two tips which likewise engage with the thread. This provides at least three clamping points between the cap and the thread, wherein the points of contact are not in the same plane and are required for the cap to sit fixedly on the thread. The additional clamping points furthermore reduce the clamping force required or enable a correspondingly higher elasticity of the cams or the surface area of the cap, so that the cap or the needle fits onto correspondingly larger and smaller thread diameters.

In a preferred embodiment of the fixing device for injection needles in accordance with the present invention, the distance between the tips of each of the notched cams is at least the height of the largest flight, whereby the cap fits onto the corresponding injection pens having a different pitch and shape of the flights without slipping or jamming.

Furthermore, in one embodiment, it is advantageous for the fixing device in accordance with the present invention if the surface area of the cap cannot be elastically deformed in its height, but rather spring elements are fixed to it which hold the notched cams. These spring elements preferably act like bending beams, a notched cam being fixed to the center-point of each, whereby its tips always engage optimally, i.e. perpendicularly, with the flights.

Although a fixing device designed in accordance with the present invention provides for improved adherence or connecting of an injection needle to a standard commercial injection apparatus, the fixing device has a complexity of design and manufacture which is usual for caps which hold an injection needle. Consequently, a fixing device for injection needles in accordance with the present invention can be manufactured just as cost-effectively and in large series as a one-piece injection-molded plastic part. Any suitable material may be used to make the fixing device. Due to its high rigidity, PCTG (polycyclohexylene-dimethylene-therephtalate) is one particularly suitable material for this application.

A particularly interesting application or use of the fixing device for injection needles in accordance with the present invention is that of ambulatory insulin treatment for diabetics, in which most injection pens are often used in various combinations, depending on the treatment. Since these injection pens have ampoules as medicine containers, which are sealed by a septum or rubber membrane, one end of the needle has to protrude into the cap, such that it pierces the septum when the cap is pushed onto the thread. Due to similar seals on the ampoules which hold the septum, these injection pens have an outer diameter of the thread or thread segment in the range of 9 to 10 mm. In accordance with one embodiment of the present invention, a cap having a correspondingly dimensioned inner diameter and at least five spring elements and notched cams, distributed at regular intervals over the circumference, fits securely onto practically any standard commercial injection pen for delivering or injecting insulin.

Any suitable injection needle may be used in accordance with the present invention. In some embodiments, the needle is preferably a 30-gauge or 31-gauge needle. In some preferred embodiments, the needle is smaller than 31-gauge.

BRIEF DESCRIPTION OF THE DRAWINGS

FIGS. 1a and 1b, is a first schematic comparison between an existing fixing device for injection needles and one embodiment of a fixing device for injection needles in accordance with the present invention;

FIGS. 2a-d, is a second schematic comparison between an existing fixing device and one embodiment of a fixing device in accordance with the present invention;

DETAILED DESCRIPTION

Figure 1:
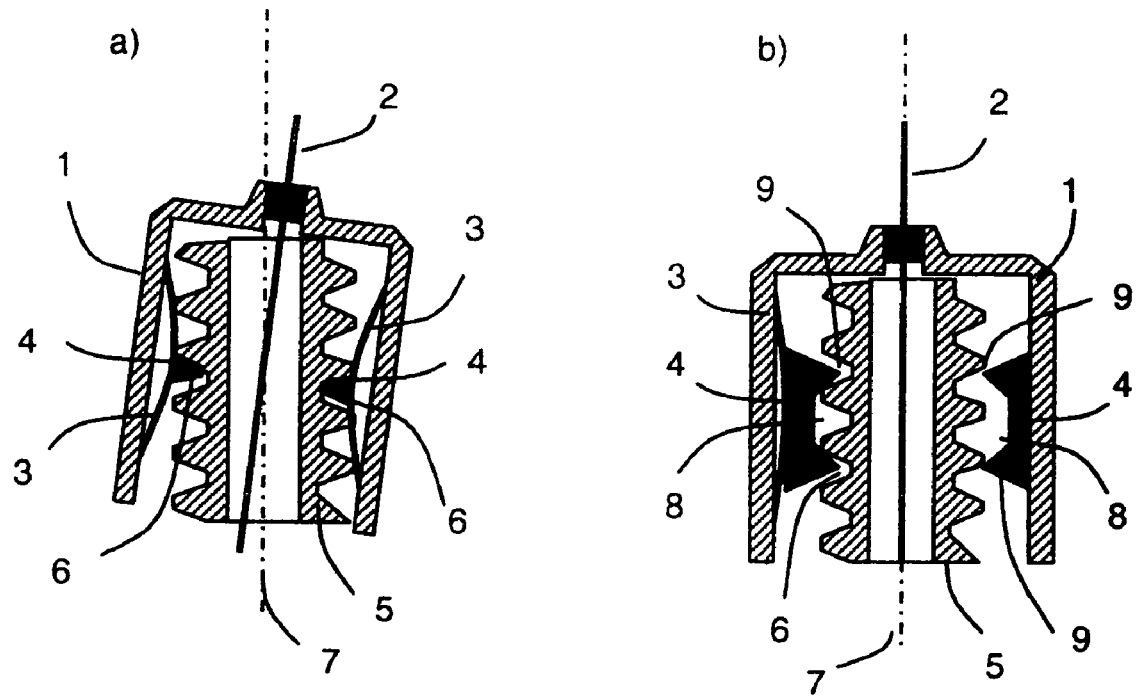
FIG. 1, including

FIG. 1 schematically shows a comparison between an existing fixing device (shown in the FIG. 1a) and a fixing device or cap 1 for a needle 2 in accordance with the present invention (shown in the FIG. 1b).

The caps 1 each have a lower, open end and an upper, closed end which holds the needle 2 perpendicular and in the middle. In some embodiments, the caps 1 comprise a continuous single wall defining a generally central, hollow cavity. Spring elements 3 are arranged like bending beams on the inner surface area of the cap 1, and a cam 4 is situated in the middle of each spring element. If the cap 1 is then turned over a thread 5, then in the existing device (FIG. 1a), the cams 4 engage with the flight 6 of the thread 5. If the positioning of the cams 4 is not adapted to the pitch of the flight 6, then the cap 1 disadvantageously tilts out of the perpendicular and/or the needle 2 is no longer parallel to the rotational axis 7 of the thread 5.

In the device in accordance with the present invention (FIG. 1b), the cams 4 are analogously attached on spring elements, but do not—as opposed to the existing cams 4—have a simple end tapering towards the thread 5. Due to a notch 8 running horizontally to the surface area of the cap 1, this end has two tips 9 which each act perpendicularly into the flight 6. The distance between the tips 9 of a cam 4 is at least the height of the flight 6, providing at least three points of contact between the fixing device or cap 1 and the thread 5, wherein said points of contact are not in the same plane. The needle 2 is thus held securely, without tilting out of the perpendicular or rotational axis 7 of the thread 5.

Figure 2:
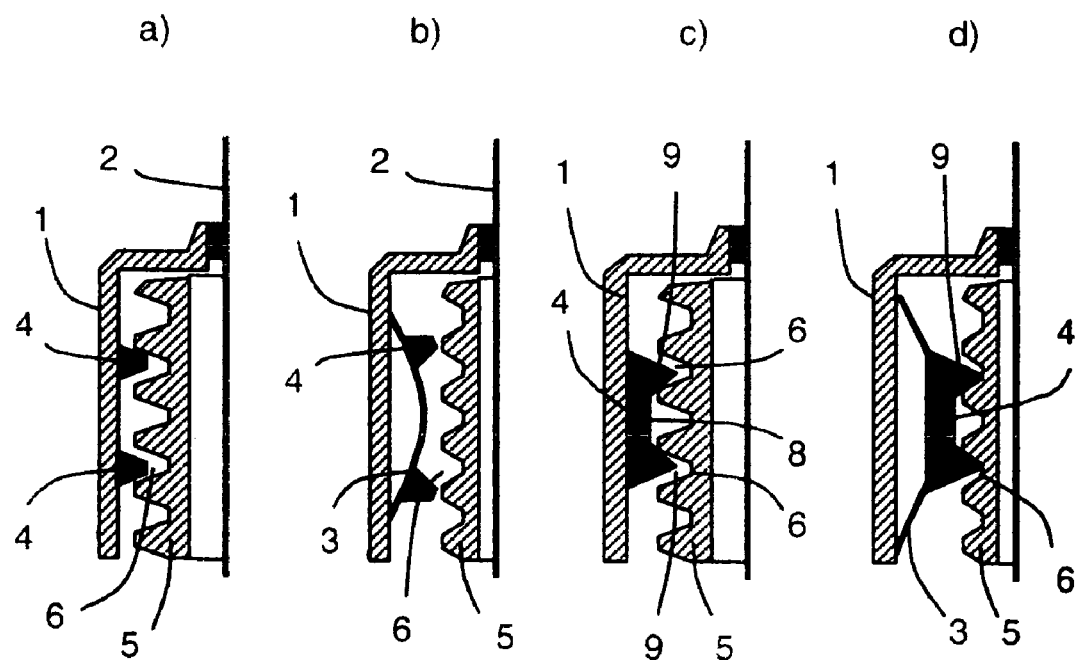
FIG. 2, including

FIG. 2 schematically shows another advantage of the fixing device or cap 1 comprising a notched cam 4 in accordance with the present invention (shown in FIGS. 2c and d), as compared to a cap 1 comprising two conventional cams 4 (shown in FIGS. 2a and b). The spring element 3 in the known solution (FIGS. 2a and b), arranged like a bending beam between the two ends of the cap 1, has two cams 4 spaced apart by at least the height of the flight 6. These cams 4 act on a thread 5 perpendicularly only, given a corresponding thread diameter, as may be seen in the FIG. 2a. In FIG. 2b, the diameter of the thread 5 is smaller, causing the spring element 3 to arch more towards the thread 5. The cams 4 situated on it tilt out of their perpendicular orientation, towards the thread, in accordance with the arching of the spring element 3. Consequently, the clamping force no longer acts optimally, i.e. perpendicularly, on the thread 5, whereby the cap 1 adheres less securely to the thread 5.

The solution in accordance with the present invention, as shown in FIGS. 2*c* and *d*), has an analogous spring element 3, acting like a bending beam, and with a cam 4 arranged on its middle. In accordance with the present invention, this cam 4 has a notch 8 and two tips 9 directed to the thread 5, whose distance is at least the height of the flight 6. Advantageously, the tips 9 or spring force always act on the thread 5 perpendicularly and with maximum spring force, even when the diameter of the thread 5 is smaller, as shown in FIG. 2*d* as compared to FIG. 2*c*.

Figure 3:
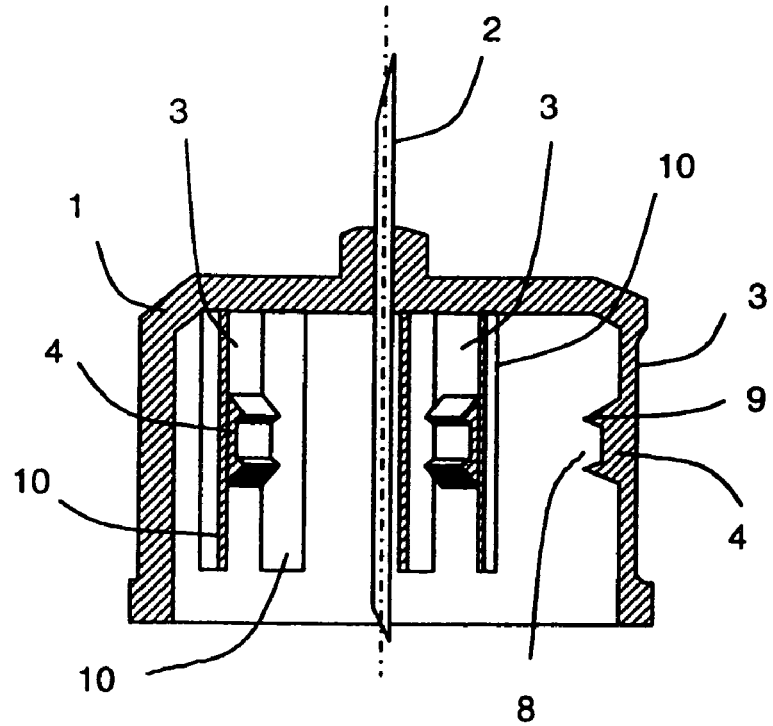
FIG. 3 is a vertical section through a fixing device in accordance with the present invention, for injection needles.

FIG. 3 shows a horizontal section through the middle of one embodiment of a fixing device for injection needles 2 in accordance with the present invention, wherein the cap 1 has segments of different thicknesses along the length of the surface area. Slits 10, which do not entirely reach from the upper to the lower end of the cap 1, separate the thinner segments from the thicker segments on both sides, enabling the thinner segments to be elastically deformed analogously to a bending beam. The spring elements 3 thus formed from the same material as the cap 1 centrally comprise a cam 4 which is a rigid swelling, formed from the same material, comprising a horizontal notch 8 and two tips 9.

Figure 4:
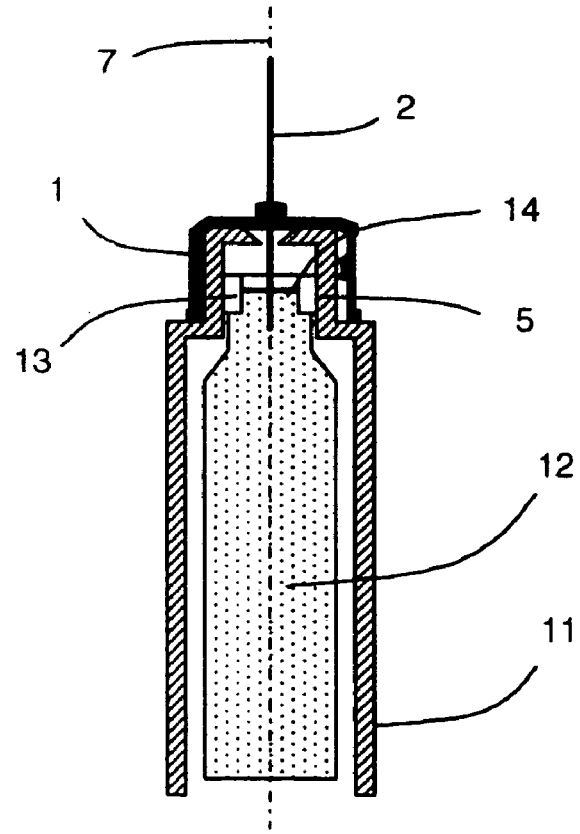
FIG. 4 is a schematic sectional drawing of a portion of an injection device in accordance with the present invention, the device comprising an injection needle, a fixing device in accordance with the present invention and the injection device (shown in part).

FIG. 4 is a schematic sectional drawing of an injection pen 11 comprising an injection needle 2 which is securely pushed or screwed onto the thread 5 with the aid of a fixing device or cap 1 in accordance with the present invention. A rotationally symmetrical ampoule 12, for example a glass or plastic cylindrical storage container filled with the medicine, is inserted in the part of the injection pen 11 provided for it. The ampoule 12 has a seal 13 at one end which conventionally protrudes into the thread 5 of the injection pen 11. One part of the seal 13 is a septum 14 or rubber membrane which is pierced by the needle 2 when the cap 1 is pushed on, if the one end of the needle 2 protrudes a corresponding distance into the interior of the cap 1. The medicine is then conveyed from the ampoule 12 into the needle 2 by a dosing means, which is not shown. After the injection pen 11 has been used, the needle or cap 1 is removed, and the septum 14 closes again.

Embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A fixing device for injection needles, for pushing onto an injection apparatus comprising a threaded segment having a plurality of threads having a pitch, wherein said fixing device is formed as a cap comprising an open lower end and a closed upper end which holds a needle perpendicularly in the middle, and a surface area of the fixing device comprises at least three spring elements fixedly connected to the cap so that the fixing device is at least slightly spring-elastic in its circumference, the spring elements each comprising a bending beam and a notched cam, each bending beam comprising a spring-elastic beam with a first end joined to the upper end of the cap and a second end joined to the lower end of the cap, and each notched cam comprising a surface substantially parallel to the surface area and tips and being fixed to a center-point of the bending beam, wherein when said fixing device is positioned on the threaded segment of the injection apparatus, the bending beams of the at least three spring elements elastically deform such that the notched cams are directed to said threaded segment and at least one of the tips of at least two of said notched cams perpendicularly engage with and provide at least three points of contact with the threaded segment.

2. The fixing device for injection needles as set forth in claim 1, wherein each cam has at least two tips which perpendicularly engage with the threaded segment.

3. The fixing device for injection needles as set forth in claim 2, wherein said tips of the notched cams provide the at least three points of contact with the injection apparatus in at least two planes.

4. The fixing device for injection needles as set forth in claim 1, wherein the distance between the tips of each notched cam is at least equal to the height of said flight.

5. The fixing device for injection needles as set forth in claim 1, wherein the surface area of the cap comprises a wall, at least a portion of which is substantially rigid so as to not be elastically deformable.

6. The fixing device for injection needles as set forth in claim 5, wherein the spring elements are segments of the surface area of the cap, made of the same material, and the bending beams are connected to the cap in a material bond at the upper and lower ends and have a wall thickness which can be elastically deformed and is correspondingly smaller than that of the rigid surface area of the wall of the cap.

7. The fixing device for injection needles as set forth in claim 6, wherein the cap, the spring elements, the bending beams and the notched cams are produced from one part.

8. The fixing device for injection needles as set forth in claim 7, wherein said one part is an injection-molded part.

9. The fixing device for injection needles as set forth in claim 8, wherein the one part is formed of a thermoplastic plastic.

10. The fixing device for injection needles as set forth in claim 9, wherein said thermoplastic plastic is PCTG (polycyclohexylene-dimethylene-therephtalate).

11. The fixing device for injection needles as set forth in claim 1, wherein the injection apparatus comprises a storage container, and wherein one end of the needle protrudes into the cap such that the one end of the needle penetrates into the storage container when the cap is pushed onto the threaded segment of the injection apparatus.

12. The fixing device for injection needles as set forth in claim 1, wherein the cap comprises a circumference and at least five spring elements with the bending beams and notched cams, said five spring elements at regular intervals around said circumference.

13. The fixing device for injection needles as set forth in claim 12, wherein the cap has an inner diameter of at least 9 mm.

14. The fixing device for injection needles as set forth in claim 1, wherein the needle is a hollow needle smaller than 30-gauge.

15. A device for connecting an injection needle to an injection apparatus comprising a threaded segment having a plurality of threads having a pitch, the device comprising spring elements, said spring elements each comprising a bending beam and a notched cam to provide tips, the bending beam comprising a spring-elastic beam with a first end joined to an upper end of the device and a second end joined to a lower end of the device, the tips joined to a central portion of the bending beams and providing a plurality of possible points of contact between the device and the injection apparatus in at least two planes, and wherein when said device is positioned on the injection apparatus, the points of contact of the tips engage with the threaded segment generally perpendicularly and spring forces of the bending beams act generally perpendicularly on the threaded segment by way of the tips such that at least three points of contact are provided between the tips and the threaded segment of the injection apparatus.

16. The device as set forth in claim 15, wherein each notched cam has at least two tips.

17. The device as set forth in claim 16, wherein said cams have a surface extending between the tips, such that the tips provide at least two points of contact which are not in the same plane.

18. The device according to claim 15, wherein the spring elements are segments of a surface area of the device.

19. The device according to claim 15, wherein the cam tips are spaced from each other by a surface, the surface having a length which is substantially the same as the height of a portion of the threaded segment of the injection apparatus.

20. The device according to claim 15, wherein at least a portion of the device is substantially rigid so as to not be elastically deformable, wherein the spring elements are segments of the device, made of the same material as the substantially rigid portion, which and wherein the bending beams are connected to the device in a material bond at the upper and lower ends and have a wall thickness which can be elastically deformed and is correspondingly less than that of the rigid portion of the device, and wherein the notched cams are made of the same material.

21. The device according to claim 15, wherein the device comprises a circumference and the spring elements are arranged at regular intervals around said circumference.

* * * * *